United States Patent [19]

Tricerri et al.

[11] Patent Number: 4,894,460
[45] Date of Patent: Jan. 16, 1990

[54] BASIC ESTERS EXHIBITING AN ANTAGONISTIC ACTIVITY TO CALCIUM, PROCESS FOR THE PREPARATION THEREOF AND PHARMACEUTICAL COMPOSITIONS THEREFROM

[75] Inventors: Silvia Z. Tricerri, Carimate; Cesare Casagrande, Arese; Franco de Marchi, Milan; Massimo Nicola, Pavia, all of Italy

[73] Assignee: Pierrel S.p.A., Napoli, Italy

[21] Appl. No.: 563,008

[22] Filed: Dec. 19, 1983

Related U.S. Application Data

[63] Continuation-in-part of Ser. No. 498,247, May 26, 1983, abandoned.

[30] Foreign Application Priority Data

Jun. 3, 1982 [IT] Italy .................................. 21678 A/82
May 11, 1983 [IT] Italy .................................. 21043 A/83

[51] Int. Cl.⁴ ........................................... C07D 401/00
[52] U.S. Cl. .................................... 544/331; 544/333; 544/364
[58] Field of Search ....................... 544/360, 364, 365; 514/252

[56] References Cited

U.S. PATENT DOCUMENTS

| | | | |
|---|---|---|---|
| 3,905,970 | 9/1975 | Bossert | 514/252 |
| 4,267,328 | 5/1981 | Najer | 544/392 |
| 4,755,512 | 7/1988 | Poindexter et al. | 544/295 |

Primary Examiner—Esther M. Kepplinger
Attorney, Agent, or Firm—Bucknam and Archer

[57] ABSTRACT

Basic esters of 1,4-dihydropyridine-3,5-dicarboxylic acid of formula (I)

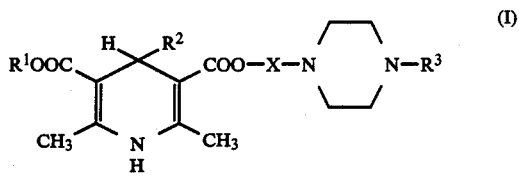

are described, in which $R^1$ is a linear or branched alkyl radical containing 1–5 carbon atoms which is unsubstituted or substituted by an alkoxy group; $R^2$ is phenyl or a nitro phenyl radical; $R^3$ is phenyl, phenyl substituted by one to three radicals selected from $(C_{1-4})$alkyl, $(C_{1-4})$alkoxy, fluoro, chloro, bromo, nitro, cyano, COOR in which R is alkyl of 1 to 4, trifluo carbon atoms, romethyl, hydroxy, amino, mono- or di-alkylamino, mono- or di-acylamino, mercapto, $S(O)_n$-alkyl with $n=0$, 1 or 2, $(C_{1-5})$acyl, carbamoyl, ureido or $R^3$ is a 5 or 6 membered heteroaryl monocyclic radical which contains one or more heteroatoms which are N, O or S such as unsubstituted pyridyl, pyrazinyl, pyrimidyl, furyl, imidazolyl, thienyl, thiazolyl, 1,2,3-triazolyl, 1,2,4-triazolyl or mono-, di- or tri-substituted with alkyl, alkoxy, halogen or trifluoromethyl; X is a linear or branched alkylen radical containing between 2 and 5 carbon atoms which is unsubstituted or substituted by an alkoxy group and their racemates, enantiomers and diastereoisomers and addition salts thereof with a pharmaceutically acceptable acid. The novel compounds exhibit calcium antagonistic activity.

2 Claims, No Drawings

BASIC ESTERS EXHIBITING AN ANTAGONISTIC ACTIVITY TO CALCIUM, PROCESS FOR THE PREPARATION THEREOF AND PHARMACEUTICAL COMPOSITIONS THEREFROM

This application is a Continuation-in-part of U.S. Pat. No. 498,247 filed May 26, 1983, now abandoned.

The present invention relates to basic esters of the general formula (I)

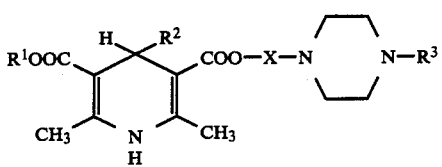

in which:

$R^1$ is a linear or branched alkyl radical containing 1–5 carbon atoms, in which one hydrogen atom may also be substituted by an alkoxy group;

$R^2$ is a phenyl or a nitrophenyl radical;

$R^3$ is phenyl, substituted or not by 1–3 radicals selected from $(C_{1-4})$alkyl, $(C_{1-4})$alkoxy, F, Cl, Br, $NO_2$, CN, COOR in which R is 1–4 carbon atoms alkyl $CF_3$, OH, $NH_2$, mono- or dialkylamino, mono- or diacylamino, SH, $S(O)_n$-alkyl with n=0, 1 or 2, $(C_1-C_5)$acyl, carbamoyl, ureido; or $R_3$ is a 5- or 6-membered heteroaryl monocyclic ring containing 1 or more N,O,S atoms; for instance, pyridyl, pyrazinyl, pyrimidyl, furyl, imidazolyl, thienyl, thiazolyl, 1,2,3-triazolyl, 1,2,4-triazolyl, optionally mono-, di- or tri-substituted with groups such as alkyl, alkoxy, halogen, trifluoromethyl;

X is an alkylene radical containing between 2 and 5 carbon atoms which may be linear or branched and in which one atom of hydrogen may also be substituted by an alkoxy group;

and related racemates, enantiomers and diastereoisomers; and their addition salts with pharmaceutically acceptable acids.

The invention also relates to the processes for the preparation of the esters of formula (I) which consist of reacting under conditions known in the art, specifically Michael addition and cyclization, the novel intermediates hereinbelow:

A. acetoacetates of formula (II)

$$CH_3-CO-CH_2-COOY \quad (II)$$

B. 3-aminocrotonates of formula (III)

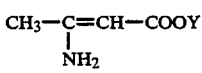

C. 2-aralykyliden-3-ketobutanoates of formula (IV)

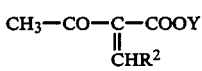

in which Y is the residue

and $R^1$, $R^2$, $R^3$ and X have the meaning indicated hereinabove, according to the reaction schemes hereinbelow:

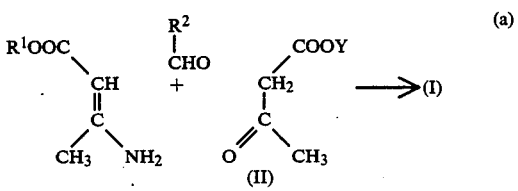

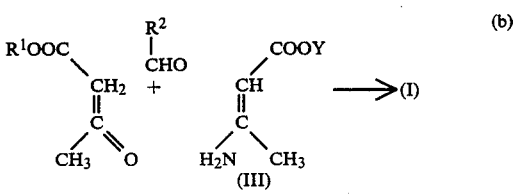

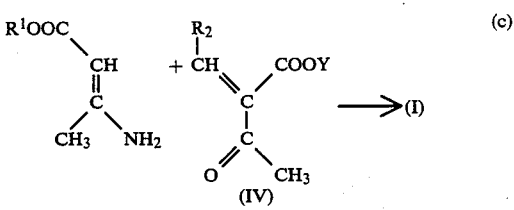

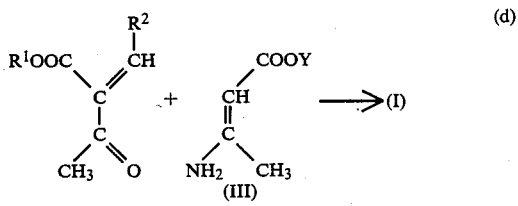

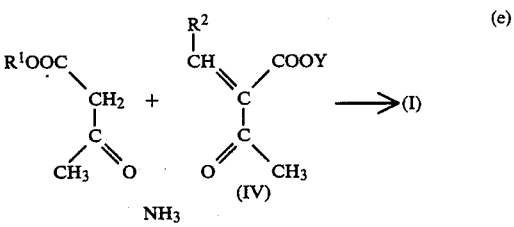

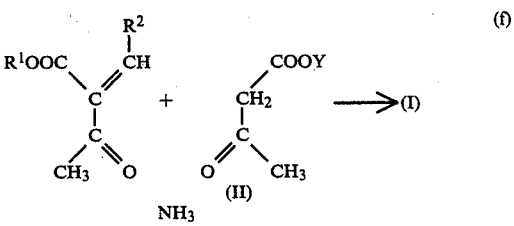

in which $R^1$, $R^2$ and Y have the meaning indicated hereinabove.

The novel basic acetoacetates of formula (II) are prepared according to a well known method from the corresponding basic alcohols and diketene. The compounds of formula (III), namely the 3-aminocrotonates, may be prepared from the intermediates of formula (II) carrying out the reaction in an alcoholic solution at about 0° C. with gaseous ammonia.

The compounds of formula (IV), that is the basic ilideneacetoacetates, may be prepared from the intermediates of formula (II) by means of a Knoevenagel condensation.

Further, the compounds of formula (I) may be obtained by reaction of a piperazine of formula (V) with a chloroalkylester of formula (VI), the latter being obtained according to a condensation and a cyclization analogous to the reaction scheme hereinabove and summarized as follows:

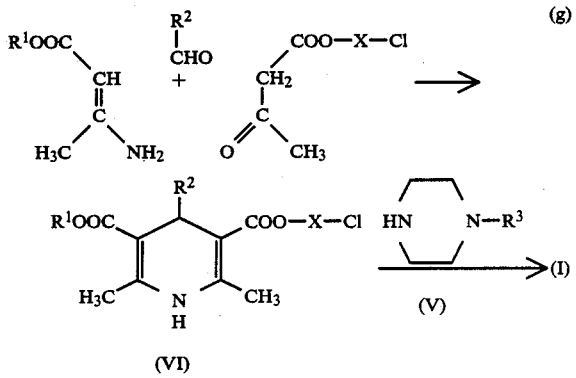

in which $R^1$, $R^2$, $R^3$ and X have the meaning indicated hereinabove.

The reaction conditions with respect to reaction schemes (a) through (g) are the same as generally used for the synthesis of 1,4-dihydropyridine. Thus, the condensation between the acetoacetates of formula (II), the aldehydes of formula $R^2$—CHO and the alkyl 3-aminocrotonates according to reaction scheme (a) is usually carried out in a lower alcohol, such as ethanol, propanol, isopropanol, etc., at the boiling temperature of the mixture, for a period of time between 2 and 20 hours. Similarly, one may proceed according to reaction schemes (b) to (f), while the reaction between the compounds of formula (V) and (VI) represented schematically in reaction scheme (g), is preferably carried out in the presence of an acid acceptor, such as triethylamine, pyridine and similar compounds.

The following examples are provided by way of illustration of the invention.

EXAMPLE 1

2-(4-Phenyl)piperazino-ethyl 2,6-dimethyl-4-(3-nitrophenyl)-5-methoxycarbonyl-1,4-dihydropyridine-3-carboxylate (code No. 0219A)

(a) To a solution of 1-phenyl-4-(2-hydroxyethyl)piperazine (20.63 g; 0.1 mole) in toluene heated to 75°-80° C., diketene (8.83 g; 0.105 moles) is added dropwise under stirring. The addition lasts about one hour. The course of the reaction is followed by HPLC. After stirring for about 2½ hours at 75°-80° C. the reaction is complete. The solvent is removed in vacuo and the residue which consists of 2-(4-phenyl)piperazino-ethyl 3-oxobutanoate, is sufficiently pure to be used without further purification; pmr (CDCL₃):δ2.23 (s, 3H, CH₃CO), 2.67 (m, 6H), 3.17 (m, 4H), 3.47 (s, 2H, COCH₂CO), 4.23 (t, 2H, OCH₂).

(b) A mixture of 32.69 g of the ketoester prepared in part a) hereinabove (0.1126 mole), 20.38 g of 3-nitrobenzaldehyde (0.135 mole) and 14.2 g of methyl 3-aminocrotonate (0.123 mole) in isopropyl alcohol (93 ml) is heated to reflux. Dissolution is complete in a few minutes and the solution is allowed to reflux for about 4 hours. The course of the reaction is followed by HPLC. A trace of insoluble material is removed by filtration and the solution is evaporated in vacuo. The oily residue, dissolved in ethyl acetate is purified by adsorption on a silica gel column followed by elution with ethyl acetate. The fractions which contain the desired product are evaporated in vacuo to dryness. The residue crystallizes from a small amount of diethyl ether in the form of pale yellow crystals, melting point 128°-130°0 C.; yield: 48%.

UV: λ238 nm (ε=36.338), λmax 352 nm (ε=7.012); pmr (CDCl₃):δ2.38 (s, 6H, =C—CH₃), 2.66 (m, 6H), 3.18 (m, 4H), 3.67 (s, 3H, OCH₃), 4.27 (t, 2H, OCH₂), 5.20 (s, 1H, C₄H), 6.47 (s, 1H, NH), 6.67-8.27 (m, 9H, CH ar).

Calculated for $C_{28}H_{32}N_4O_6$ (520.59) %: C, 64.60; H, 6.18; N, 10.76. Found: C, 64.48; H, 6.28; N, 10.92.

EXAMPLE 2

2-[4-(2-Thiazolyl)]piperazino-ethyl 2,6-dimethyl-4-(3-nitrophenyl)-5-methoxycarbonyl-1,4-dihydropyridine-3-carboxylate (code No. 0240A)

By following essentially the same procedure of Example 1 and using 2-[4-(2-thiazolyl)-1- piperazinyl]ethyl 3-oxo-butanoate, after recrystallization from diethyl ether, a pale yellow product of m.p. 155°-157° C. is obtained. UV:λ237 nm (ε=29.536), λ263 nm (ε=19.562), λmax 352 nm (ε=7.131), pmr (CDCl₃):δ2.37 (s, 6H, =C—CH₃), 2.63 (m, 6H), 3.43 (t, 4H), 3.67 (s, 3H, OCH₃), 4.23 (t, 2H, OCH₂), 5.13 (s, 1H, C₄H), 6.53 (s, 1H, NH), 6.58 (d, 1H =CH—S), 7.17 (d, 1H,=CH—N), 7.27-8.23 (m, 4H, =CH ar).

Calculated for $C_{25}H_{29}N_5O_6S$%: C, 56.91; H, 5.54; N, 13.27. Found: C, 56.77; H, 5.64; N, 13.18.

EXAMPLE 3

[2-[4-(2-pyrimidyl)]-piperazino-ethyl 2,6-dimethyl-4-(3-nitrophenyl)-5-methoxycarbonyl-1,4-dihydropyridine-3-carboxylate (code No. 0241A)

From 3-nitrobenzaldehyde, methyl 3-aminocrotonate and ethyl 2-[4-(2-pyrimidyl)-1-piperazinyl]-3-oxobutanoate in refluxing isopropyl alcohol a pale yellow solid is obtained after purification through the hydrochloride and regeneration of the base. After recrystallization from ethyl ether, it melts at 145°-147° C.;

UV: λ240 nm (ε=48.086), λmax 348 nm (ε=7.135); pmr (CDCl₃)-δ2.37 (s, 6H, =C—CH₃), 2.60 (m, 6H), 3.67 (s, 3H, OCH₃), 3.80 (t, 4H), 4.23 (t, 2H, OCH₂), 5.13 (s, 1H, C₄H), 6.23 (s, 1H, NH), 6.47 (t, 1H =CH pyrim), 7.17-8.20 (m, 4H, =CH ar), 8.30 (d, 2H, =CH pyrim).

Calculated for $C_{26}H_{30}N_6O_6$ (522.56)%: C, 59.76; H, 5.79; N, 16.07. Found: C, 59.62; H, 5.88; N, 16.28.

EXAMPLE 4

2-[4-(2-Methoxyphenyl)]-piperazino-ethyl 2,6-dimethyl-4-(3-nitrophenyl)-5-methoxycarbonyl-1,4-dihydropyridine-3-carboxylate (code No. 0242A)

By following the same procedure of Example 1 and by using 2-[4-(2-methoxyphenyl)-piperazinyl]ethyl 3-oxobutanoate, a pale yellow solid, m.p. 157°-158° C. is obtained, after recrystallization from diethyl ether.

UV: λ237 nm (ε=34.261), λmax 352 nm (ε=6.916); pmr (CDCl$_3$):δ2.37 (s, 6H, =C—CH$_3$), 2.67 (m, 6H), 3.03 (m, 4H), 3.67 (s, 3H, COOCH$_3$), 3.87 (s, 3H, =C—OCH$_3$), 4.23 (t, 2H, OCH$_2$), 5.13 (s, 1H, C$_4$H), 6.07 (s, 1H, NH), 6.93 (s, 4H, =CH ar), 7.17–8.20 (m, 4H, =CH ar).

Calculated for C$_{29}$H$_{34}$N$_4$O$_7$ (550.62)%: C, 63.26; H, 6.22; N, 10.17 Found: C, 63.09; H, 6.27; N, 9.95.

EXAMPLE 5

2-[4-(2-Tolyl)]piperazino-ethyl 2,6-dimethyl-4-(3-nitrophenyl)-5-methoxycarbonyl-1,4-dihydropyridine-3-carboxylate (code No. 0243A)

By following the same procedure as in Example 1, and starting from 2-[4-(2-tolyl-1-piperazinyl)ethyl 3-oxobutanoate, a crude material is obtained, which is purified through the hydrochloride and regenerating the base. After recrystallization from diethyl ether, the m.p. is 155°–157° C.; uv: λ237 nm (ε=34.780), λmax 352 nm (ε=7.268); pmr (CDCl$_3$): δ2.27–2.38 (3s, 9H, =C—CH$_3$), 2.43–3.07 (2m, 10H), 3.67 (s, 3H, OCH$_3$), 4.23 (t, 2H, OCH$_2$), 5.16 (s, 1H, C$_4$H), 6.27 (s, 1H, NH), 6.73–8.23 (m, 8H, =CH ar).

Calculated for C$_{29}$H$_{34}$N$_4$O$_6$ (534.62)%: C, 65.15; H, 6.41; N, 10.47. Found: C, 65.02; H, 6.51; N, 10.05.

EXAMPLE 6

2-(4-Phenyl)piperazino-ethyl 2,6-dimethyl-4-(3-nitrophenyl)-5-methoxycarbonyl-1,4-dihydropyridine-3-carboxylate (code No. 0219A)

(a) A mixture of 2-chloroethyl acetoacetate (18.53 g, 112 mmol), 3-nitrobenzoldehyde (20.38 g, 134 mmol) and methyl 3-aminocrotonate (14.2 g, 123 mmol) in 93 ml of isopropanol is heated under reflux for 4 hours. The reaction mixture is then evaporated to dryness and the residue, dissolved in a small amount of methylene chloride, is chromatographed over a silica gel column using methylene chloride as the eluent.

The fractions containing the desired product are combined, the solvent evaporated and the residue recrystallized from diethyl ether and isopropyl ether in the ratio 1:1 to give 16 g (36%) of 2-chloroethyl 5-carbomethoxy-1,4-dihydro-2,6-dimethyl-4-(3-nitrophenyl)-3-pyridinecarboxylate; m.p. 130°–132° C. [Lit.: 130°–131° C. (M. Iwanami et al., Chem. Pharm. Bull. 27, 1426 (1979)].

From the chromatographic column after subsequent elution with ethyl acetate, a more polar product is isolated which results to be 2-hydroxyethyl 2,6-dimethyl-4-(3-nitrophenyl)-5-methoxycarbonyl-1,4-dihydropyridine-3-carboxylate (described in German Offenlegungsschrift 2.629.892).

The following intermediates are prepared by analogous procedures:

2-chloroethyl 2,6-dimethyl-4-(3-nitrophenyl)-5-ethoxycarbonyl-1,4-dihydropyridine-3-carboxylate, yield 79%; m.p. 150°–153° C. (Chem. Pharm. Bull. 27, 1426 (1979));

2-chloroethyl 2,6-dimethyl-4-(3-nitrophenyl)-5-(2-methoxy)ethoxy-crbonyl-1,4-dihydropyridine-3-carboxylate, yield 61%; m.p. 136°–139° C.

2-chloroethyl 2,6-dimethyl-4-(3-nitrophenyl)-5-isobutoxycarbonyl-1,4-dihydropyridine-3-carboxylate, yield 26%; m.p. 150°–153° C;

the analytical and spectroscopic data of these compounds are in agreement with the indicated structure.

(b) A mixture of 2-chloroethyl-5-carbomethoxy-1,4-dihydro-2,6-dimethyl-4-(3-nitrophenyl)-3-pyridinecarboxylate (3.95 g, 10 mmol), 1-phenylpiperazine (1.62 g, 10 mmol), triethylamine (1.45 ml, 10 mmol) and sodium iodide (1.5 g, 10 mmol) in 40 ml of isopropanol is heated under reflux for 4 hours. After standing one night, the reaction mixture is evaporated to dryness and the residue, dissolved in 100 ml of methylene chloride, is washed with water and dried (Na$_2$SO$_4$).

The oil obtained after evaporation of the solvent (8 g) is purified by silica gel column chromatography eluting with mixtures of ethyl acetate and methylene chloride with increasing amounts of ethyl acetate.

The fractions which contain the desired product are concentrated and the residue is crystallized from diethyl ether to afford 2.35 g (45.2%); m.p. 128°–130° C., identical to the product of Example 1.

By following essentially the same procedures of the previous examples and using as starting materials the appropriate intermediates, the products which, together with the products described hereinabove, are summarized in Table I are obtained.

TABLE I

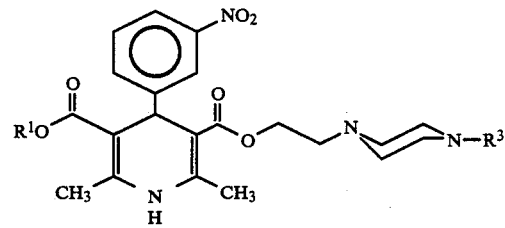

I

| Code No. | R$^1$ | R$^3$ | m.p. | Empyrical Formula | Microanalysis C Calc. Found % | H Calc. Found % | N Calc. Found % |
|---|---|---|---|---|---|---|---|
| 0219A | CH$_3$ | C$_6$H$_5$ | 128–130° | C$_{28}$H$_{32}$N$_4$O$_6$ | 64.60–64.48 | 6.20–6.29 | 10.76–10.51 |
| 0248B | CH$_3$ | 2-Cl—C$_6$H$_4$ | 147–149° | C$_{28}$H$_{31}$ClN$_4$O$_6$ | 60.58–60.58 | 5.63–5.75 | 10.09–9.93 |
| 0255B | CH$_3$ | 3-Cl—C$_6$H$_4$ | 117° | C$_{28}$H$_{31}$ClN$_4$O$_6$ | 60.59–60.44 | 5.63–5.71 | 10.09–9.93 |
| 0264B | CH$_3$ | 4-Cl—C$_6$H$_4$ | 141–143° | C$_{28}$H$_{31}$ClN$_4$O$_6$ | 60.59–60.43 | 5.63–5.71 | 10.09–9.99 |
| 0250B | CH$_3$ | 4-F—C$_6$H$_4$ | 128–130° | C$_{28}$H$_{31}$FN$_4$O$_6$ | 62.44–62.30 | 5.80–5.87 | 10.40–10.24 |
| 0249B | CH$_3$ | 3-CF$_3$—C$_6$H$_4$ | 134–135° | C$_{29}$H$_{31}$F$_3$N$_4$O$_6$ | 59.18–59.03 | 5.31–5.40 | 9.52–9.41 |
| 0242A | CH$_3$ | 2-OCH$_3$—C$_6$H$_4$ | 157–158° | C$_{29}$H$_{34}$N$_4$O$_7$ | 63.26–63.35 | 6.22–6.18 | 10.18–10.29 |
| 0266B | CH$_3$ | 4-OCH$_3$—C$_6$H$_4$ | 167–169° | C$_{29}$H$_{34}$N$_4$O$_7$ | 63.26–63.07 | 6.22–6.30 | 10.18–9.98 |
| 0243A | CH$_3$ | 2-CH$_3$—C$_6$H$_4$ | 155–157° | C$_{29}$H$_{34}$N$_4$O$_6$ | 65.15–65.28 | 6.41–6.38 | 10.48–10.55 |
| 0240A | CH$_3$ | 2-thiazolyl | 156–157° | C$_{25}$H$_{29}$N$_5$O$_6$S | 56.91–57.08 | 5.54–5.60 | 13.27–13.20 |

TABLE I-continued

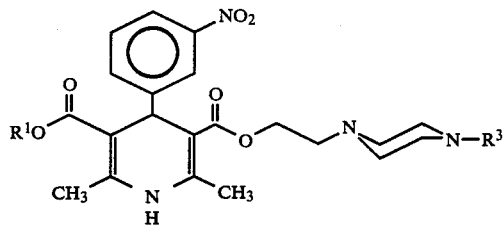

| Code No. | R¹ | R³ | m.p. | Empyrical Formula | Microanalysis C Calc. Found % | H Calc. Found % | N Calc. Found % |
|---|---|---|---|---|---|---|---|
| 0241A | CH₃ | 2-pyrimidyl | 145–147° | C₂₆H₃₀N₆O₆ | 59.76–59.85 | 5.79–5.88 | 16.08–16.00 |
| 0251B | CH₃ | 2-pyridyl | 132° | C₂₇H₃₁N₅O₆ | 62.18–62.21 | 5.99–6.06 | 13.43–13.51 |
| 0285C | CH₃ | 3,4-(Cl)₂—C₆H₃ | 166–169° | C₂₈H₃₀Cl₂N₄O₆ | 57.05–56.82 | 5.13–5.15 | 9.50–9.27 |
| 0288C | CH₃ | 3,4-(CH₃)₂—C₆H₃ | 182–183° | C₃₀H₃₆N₄O₆ | 65.69– | 6.60– | 10.21– |
| 0284C | C₂H₅ | 4-F—C₆H₄ | 124–127° | C₂₉H₃₃FN₄O₆ | 63.03–62.94 | 6.02–6.08 | 10.14–9.95 |
| 0283C | CH₂CH₂OCH₃ | 4-F—C₆H₄ | 105–107° | C₃₀H₃₅FN₄O₇ | 61.84–61.84 | 6.05–6.08 | 9.62–9.49 |
| 0282C | CH₂CH(CH₃)₂ | 4-F—C₆H₄ | 115–118° | C₃₁H₃₇FN₄O₆ | 64.12–63.99 | 6.42–6.58 | 9.65–9.48 |
| 0289C | CH₂CH(CH₃)₂ | C₆H₅ | 98–99° | C₃₁H₃₈N₄O₆ | 66.17–66.67 | 6.81–6.97 | 9.96–10.31 |
| 0290C | CH₂CH₂OCH₃ | C₆H₅ | 107–109° | C₃₀H₃₆N₄O₇ | 63.82–63.95 | 6.41–6.48 | 9.92–10.18 |
| 0291C | CH₂CH₃ | C₆H₅ | 103–105° | C₂₉H₃₄N₄O₆ | 65.15–65.55 | 6.41–6.50 | 10.48–10.65 |
| 0292C | CH₂CH(CH₃)₂ | 4-Cl—C₆H₄ | 164–165° | C₃₁H₃₇ClN₄O₂ | 62.36–62.70 | 6.25–6.36 | 9.38–9.48 |
| 0293C | CH₂CH₂OCH₃ | 4-Cl—C₆H₄ | 134–135° | C₃₀H₃₅ClN₄O₇ | 60.15–60.83 | 5.89–6.15 | 9.35–9.58 |
| 0294C | CH₂CH₃ | 4-Cl—C₆H₄ | 123–125° | C₂₉H₃₃ClN₄O₆ | 61.21–61.93 | 5.84–5.98 | 9.85–10.24 |
| 0295C | CH₃ | 4-NO₂—C₆H₄ | 200–202° | C₂₈H₃₁N₅O₈ | 59.46–59.53 | 5.52–5.72 | 12.38–11.89 |
| 0296C | CH₃ | 3-CF₃—4-NO₂—C₆H₄ | 134–136° | C₂₉H₃₀F₃N₅O₈ | 54.98–55.34 | 4.77–5.08 | 11.05–10.77 |
| 0297C | CH₃ | 4-CF₃C₆H₄ | 119–122° | C₂₉H₃₁F₃N₄O₆ | 59.18–58.78 | 5.31–5.38 | 9.52–10.08 |
| 0298C | CH₃ | 3-CH₃O—C₆H₄ | 146–147° | C₂₈H₃₄N₄O₇ | 63.26–63.27 | 6.22–6.28 | 10.17–9.96 |
| 0289C | CH₂CH(CH₃)₂ | C₆H₅ | 98–99° | C₃₁H₃₈N₄O₆ | 66.17–66.67 | 6.81–6.97 | 9.96–10.31 |
| 0290C | CH₂CH₂OCH₃ | C₆H₅ | 107–109° | C₃₀H₃₆N₄O₇ | 63.82–63.95 | 6.41–6.48 | 9.92–10.18 |
| 0291C | CH₂CH₃ | C₆H₅ | 103–105° | C₂₉H₃₄N₄O₆ | 65.15–65.55 | 6.41–6.50 | 10.48–10.65 |
| 0292C | CH₂CH(CH₃)₂ | 4-Cl—C₆H₄ | 164–165° | C₃₁H₃₇ClN₄O₆ | 62.36–62.70 | 6.25–6.36 | 9.38–9.48 |
| 0293C | CH₂CH₂OCH₃ | 4-Cl—C₆H₄ | 134–135° | C₃₀H₃₅ClN₄O₇ | 60.15–60.83 | 5.89–6.15 | 9.35–9.58 |
| 0294C | CH₂CH₃ | 4-Cl—C₆H₄ | 123–125° | C₂₉H₃₃ClN₄O₆ | 61.21–61.93 | 5.84–5.98 | 9.85–10.24 |
| 0295C | CH₃ | 4-NO₂—C₆H₄ | 200–202° | C₂₈H₃₃N₅O₈ | 59.46–59.53 | 5.52–5.72 | 12.38–11.89 |
| 0296C | CH₃ | 3-CF₃—4-NO₂—C₆H₄ | 134–136° | C₂₉H₃₀F₃N₅O₈ | 54.98–55.34 | 4.77–5.08 | 11.05–10.77 |
| 0297C | CH₃ | 4-CF₃G₆H₄ | 119–122° | C₂₉H₃₁F₃N₄O₆ | 59.18–58.78 | 5.31–5.38 | 9.52–10.08 |
| 0298C | CH₃ | 3-CH₃O—C₆H₄ | 146–147° | C₂₈H₃₄N₄O₇ | 63.26–63.27 | 6.22–6.28 | 10.17–9.96 |

The names of some of the compounds are:
0289C 2-(4-Phenyl)piperazinoethyl-2,6-dimethyl-4-(3-nitrophenyl)-5-isobutoxycarbonyl-1,4-dihydropyridine-3-carboxylate
0290C 2-(4-Phenyl)piperazinoethyl-2,6-dimethyl-4-(3-nitrophenyl)-5-(2-methoxy)ethoxycarbonyl-1,4-dihydropyridine-3-carboxylate
0291C 2-[(4-Phenyl)piperazinoethyl-2,6-dimethyl-4-(3-nitrophenyl)-5-ethoxycarbonyl-1,4-dihydropyridine-3-carboxylate
0292C 2-[4-(4-Chlorophenyl)]piperazinoethyl-2,6-dimethyl-4-(3-nitrophenyl)-5-isobutoxycarbonyl-1,4-dihydropyridine-3-carboxylate
0293C 2-[4-(4-Chlorophenyl)]piperazinoethyl-2,6-dimethyl-4-(3-nitrophenyl)-5-(2-methoxy)ethoxycarbonyl-1,4-dihydropyridine-3-carboxylate
0294C 2-[4-(4-Chlorophenyl)]piperazinoethyl-2,6-dimethyl-4-(3-nitrophenyl)-5-ethoxycarbonyl-1,4-dihydropyridine-3-carboxylate
0295C 2-[4-(4-Nitrophenyl)]piperazinoethyl-2,6-dimethyl-4-(3-nitrophenyl)-5-methoxycarbonyl-1,4-dihydropyridine-3-carboxylate
0296C 2-[4-(3-Trifluoromethyl-4-nitrophenyl)]piperazinoethyl-2,6-dimethyl-4-(3-nitrophenyl)-5-methoxycarbonyl-1,4-dihydropyridine-3-carboxylate
0297C 2-[4-(4-Trifluoromethylphenyl)]piperazinoethyl-2,6-dimethyl-4-(3-nitrophenyl)-5-methoxycarbonyl-1,4-dihydropyridine-3-carboxylate
0298C 2-[4-(3-Methoxyphenyl)]piperazinoethyl-2,6-dimethyl-4-(3-nitrophenyl)-5-methoxycarbonyl-1,4-dihydropyridine-3-carboxylate The names of some of the compounds are:
0289C 2-(4-Phenyl)piperazinoethyl-2,6-dimethyl-4-(3-nitrophenyl)-5-isobutoxycarbonyl-1,4-dihydropyridine-3-carboxylate
0290C 2-(4-Phenyl)piperazinoethyl-2,6-dimethyl-4-(3-nitrophenyl)-5-(2-methoxy)ethoxycarbonyl-1,4-dihydropyridine-3-carboxylate
0291C 2-[(4-Phenyl)piperazinoethyl-2,6-dimethyl-4-(3-nitrophenyl)-5-ethoxycarbonyl-1,4-dihydropyridine-3-carboxylate
0292C 2-[4-(4-Chlorophenyl)]piperazinoethyl-2,6-dimethyl-4-(3-nitrophenyl)-5-isobutoxycarbonyl-1,4-dihydropyridine-3-carboxylate
0293C 2-[4-(4-Chlorophenyl)]piperazinoethyl-2,6-dimethyl-4-(3-nitrophenyl)-5-(2-methoxy)ethoxycarbonyl-1,4-dihydropyridine-3-carboxylate
0294C 2-[4-(4-Chlorophenyl)]piperazinoethyl-2,6-dimethyl-4-(3-nitrophenyl)-5-ethoxycarbonyl-1,4-dihydropyridine-3-carboxylate
0295C 2-[4-(4-Nitrophenyl)]piperazinoethyl-2,6-dimethyl-4-(3-nitrophenyl)-5-methoxycarbonyl-1,4-dihydropyridine-3-carboxylate
0296C 2-[4-(3-Trifluoromethyl-4-nitrophenyl)-]piperazinoethyl-2,6-dimethyl-4-(3-nitrophenyl)-5-methoxycarbonyl-1,4-dihydropyridine-3-carboxylate
0297C 2-[4-(4-Trifluoromethylphenyl)]piperazinoethyl-2,6-dimethyl-4-(3-nitrophenyl)-5-methoxycarbonyl-1,4-dihydropyridine-3-carboxylate
0298C 2-[4-(3-Methoxyphenyl)]piperazinoethyl-2,6-dimethyl-4-(3-nitrophenyl)-5-methoxycarbonyl-1,4-dihydropyridine-3-carboxylate Other compounds falling within the scope of the present invention which may be obtained, according to the reaction schemes indicated hereinabove, starting from the appropriate intermediates, are as follows:
2-(4-phenyl)piperazino-ethyl 2,6-dimethyl-4-(2-nitrophenyl)-5-methoxycarbonyl-1,4-dihydropyridine-3-carboxylate;

2-(4-phenyl)piperazino-ethyl 2,6-dimethyl-4-(4-nitrophenyl)-5-ethoxycarbonyl-1,4-dihydropyridine-3-carboxylate;

2-[4-(4-fluorophenyl)]-piperazino-ethyl 2,6-dimethyl-4-(2-nitrophenyl)-5-isobutoxycarbonyl-1,4-dihydropyridine-3-carboxylate;

2-[4-(2-pyrimidyl)]piperazino-ethyl 2,6-dimethyl-4-(2-nitrophenyl)-5-methoxycrbonyl-1,4-dihydropyridine-3-carboxylate;

3-(4-phenyl)piperazino-propyl 2,6-dmethyl-4-(2-nitrophenyl)-5-(2-methoxy)ethoxycarbonyl-1,4-dihydropyridine-3-carboxylate;

2-[4-(4-trifluoromethylphenyl)]piperazino-ethyl 2,6-dimethyl-4-(4-nitrophenyl)-5-isopropoxycarbonyl-1,4-dihydropyridine-3-carboxylate.

The compounds of the present invention have been evaluated in a series of pharmacological tests, the methods and results of which are summarized hereinbelow.

Intravenous Toxicity in Mice

Male CD1 mice from Charles River (Italy), weighing 25 g were used. Compounds were administered intravenously (i.v.), dissolved in dimethylsulfoxide, and the volume of administration was 0.01 ml per 10 g of body weight. The $LD_{50}$ after seven days, was calculated according to the method of Litchfield and Wilcoxon (Experimental Therapeutics 96, 99 (1949)).

Antagonistic Activity to Calcium in the Taenia Coli of Guinea Pigs

Hartley albino guinea pigs of average weight 450 g were used. The calcium antagonistic activity was determined stimulating the taenia coli, previously depolarized, with a single submaximal concentration of $CaCl_2$ ($10^{-3}M$), at intervals of 20 minutes (according to the method Naunyn Schmied. Arch. Pharmacol. 318, 235 (1982)). The products were left in contact with the preparation for 10 minutes. The $ED_{50}$ were calculated from the percentage of maximum inhibition.

Hypotensive Activity in Spontaneous Hypertensive Rats (SHR)

Male SHR (Okamoto), of 70-100 days of age were used. The systolic arterial pressure (SABP) was determined by applying to the tail of the animal a pressure transducer with a sleeve connected to a BP-Recorder (W-W Electronic of Basel). The animals were previously warmed to 39° C. for a period of 15-20 minutes in a ventilated chamber.

The rats were previously trained to the registration for 1-2 days prior to the start of the experiment which consisted of a basic registration, the pharmacological treatment and then of subsequent registrations one hour and three hours after the treatment.

All the products were administered orally (p.o.), suspended in 0.4% carboxymethyl cellulose (Methocel); the volume of vehicle was 2 ml per kg.

The compounds of formula (I) were tested at three dose levels and the value of ED-25% was determined.

RESULTS

The results are summarized in Table III. The compounds according to the invention exhibit a calcium antagonistic activity and are therefore useful for the treatment and for the prophylaxis of hypertension, of the various forms of angina, in ischemia and in other cardiovascular pathologies.

With the only exception of compound 0241A, the compounds produce inhibition of contractions due to $CaCl_2$ which increases progressively in spite of repeated washing of the tissue.

The effect of the compound 0241A and Nifedipine, on the contrary, is readily reversible when the contact between the product and the tissue is interrupted. Due to this phenomenon of inhibition even after the tissue is washed, the determination of $ED_{50}$ was made taking into consideration the maximum inhibition, which is achieved independently from the time of appearance. The hypotensive activity is comparable to the activity of Nifedipine except for the compounds which are substituted with halogen (0248B, 0255B, 0246B, 0250B, 0249B), which exhibit superior activity.

In the case of some of the latter compounds (0264B, 0250B and 0249B), the hypotensive activity is still present after 30 hours and is about twice the activity of Nifedipine.

With respect to the toxicity, the compounds of formula (I) are generally less toxic than Nifedipine.

Compared to Nicardipine, the compounds of formula (I) exhibit a calcium antagonistic activity of equivalent potency but longer duration in the in vitro test.

TABLE II

In vitro calcium antagonistic activity (taenia coli), antihypertensive activity in SHR and acute toxicity in mice of the compounds of formula (I)

| Code No. | $LD_{50}$ mice i.v. (mg/kg) | Calcium antagonistic activity in vitro $ED_{50}$ $\times 10^{-9}$ M | Hypotensive activity in SHR (mg/kg p.o.) $ED^{SABP}$ $-25\%$ |
|---|---|---|---|
| 0219A | 8.6 (5.1–14.5) | 2.4 | 8.7 |
| 0248B | 24.7 (18.7–32.6) | 3 | 13.8 |
| 0255B | 25.5 (19.5–33.4) | 3.5 | 6.3 |
| 0264B | 32.1 (18.7–26.1) | 6.4 | 6.3 |
| 0250B | 17.7 (12.4–25.3) | 2.5 | 7.5 |
| 0249B | 35.3 (27.2–45.6) | 22 | 6.6 |
| 0242A | 2.9 (2.1–3.8) | 3.4 | 13.8 |
| 0266B | 22.7 (18.4–27.9) | 3.6 | 10.7 |
| 0243A | 14.7 (10.35–20.9) | 1.9 | 6.6 |
| 0240A | 7.1 (5.0–10.0) | 4.2 | 31 |
| 0241A | 34.6 (29.8–10.1) | 4.6 | 72 |
| 0251B | 12.6 (10.3–15.4) | 4.6 | 34 |
| 0285C | 39.0 (29.6–51.3) | 10.5 | 10.2 |
| 0284C | 9.5 (7.9–11.4) | 1.3 | 5.3 |
| 0283C | 7.8 (6.9–8.9) | 2.6 | 8.3 |
| 0282C | 27.5 (24.1–31.4) | 4.9 | 3.9 |
| Nifedipine | 10.8 (9.2–12.8) | 2.6 | 25 |
| Nicardipine | 17.4 (11.0–27.5) | 2.3 | 8.6 |
| Nitrendipine | 34.5 (32.5–36.5) | 1.9 | — |
| 0289C | 12 | 6.3 | 2.2 |
| 0290C | 7.5 | 3 | 16.7 |
| 0291C | 25 | 3.9 | 6.6 |
| 0292C | 35 | 94 | 11.7 |
| 0293C | 16 | 4.1 | 10.5 |
| 0294C | 19 | 5.1 | 4.2 |
| 0295C | 38 | 11 | >20 |
| 0296C | 55 | 19 | 87 |
| 0297C | 73 | 15 | 4.4 |
| 0298C | 38 | 7.5 | 32 |

The present invention also covers all the industrial aspects connected with the therapeutical use of the esters of formula (I). Thus, an essential aspect of the invention includes the pharmaceutical formulations containing predetermined amounts of the esters and their salts. The compounds according to the invention may be administered by oral route or by parenteral route, for instance in the form of tablets, capsules, small envelopes, containing hydrodispersable powders and vials for injection. The compounds of the invention can be administered in humans 1-3 times a day at doses of 5-50 mg.

We claim:

1. The compound 2[4-(2-thiazolyl)]piperazino-ethyl 2,6-dimethyl-4-(3-nitrophenyl)-5-methoxycarbonyl-1,4-dihydropyridine-3-carboxylate.

2. The compound 2-[4-(2-pyrimidyl)]piperazino-ethyl 2,6-dimethyl-4-(3-nitrophenyl)-5-methoxycarbonyl-1,4-dihydropyridine-3-carboxylate.